(12) United States Patent
Okushin

(10) Patent No.: US 6,667,033 B1
(45) Date of Patent: Dec. 23, 2003

(54) THERAPEUTIC AGENT FOR CHRONIC HEPATITIS B

(76) Inventor: Hiroaki Okushin, 605, 12-12, Nishiyachiyocho, Himeji-shi, Hyogo 670-0876 (JP)

( * ) Notice: Subject to any disclaimer, the term of this patent is extended or adjusted under 35 U.S.C. 154(b) by 234 days.

(21) Appl. No.: 09/339,239

(22) Filed: Jun. 24, 1999

(30) Foreign Application Priority Data

Jun. 24, 1998 (JP) ............................................. 10-176851

(51) Int. Cl.⁷ ........................ A61K 38/21; A61K 45/00; A61K 38/00; C07K 17/00; C07K 14/00
(52) U.S. Cl. ................... 424/85.6; 424/85.1; 424/85.4; 424/85.7; 514/2; 530/350; 530/351
(58) Field of Search ............................. 514/2; 530/350, 530/351; 424/85.6, 85.7, 85.4, 85.1

(56) References Cited

PUBLICATIONS

Krogsgaard et al. (J. Hepatology, 1996, 25(6), pp. 795–802).*
Park et al. (Gastroenterology, 1996, 110(4 suppl.), p. A1290),.*
Eisenberg et al. (Antinincrob. Agents Chenother., 1986, 29(1), pp. 122–126).*
Chiang et al. (J. Interferon Res., 1993, 13(2), pp. 111–120.*

* cited by examiner

Primary Examiner—Yvonne Eyler
Assistant Examiner—Janet L. Andres
(74) Attorney, Agent, or Firm—Crowell & Moring LLP

(57) ABSTRACT

The present invention provides an effective method for treating chronic hepatitis B. Specifically, the present invention provides a method for treating chronic hepatitis B wherein interferon (IFN) is divided and administered in 2 to 4 portions per day and its total dosage is the daily effective dosage of IFN. The IFN is IFN-α or IFN-β.

6 Claims, No Drawings

THERAPEUTIC AGENT FOR CHRONIC HEPATITIS B

BACKGROUND OF THE INVENTION

The present invention relates to a therapeutic agent for persistent disappearance (persistent seronegative) of hepatitis B virus (HBV)-DNA in treating chronic hepatitis B.

In particular, the present invention relates to a therapeutic agent for chronic hepatitis B, which induces the conversion of HBe antigen positive to HBe antibody positive (seroconversion), thus efficiently affecting the persistent disappearance of HBV-DNA via a drug administration system (unit) using said therapeutic agent.

Hepatitis B caused by hepatitis B virus (herein after stated as HBV) includes 2 types of hepatitis, acute hepatitis caused by infection in adults (first infection in adults) and chronic hepatitis in the state of persistent infection (carrier) with first infection occuring between a mother and baby, or during the infant stage.

Among these, the first infection in adults causes severe conditions in some, but in many cases, the virus is excluded and the hepatitis is thereby treated, so there is no necessity for antiviral therapy. On the other hand, three types of hepatopathy are observed in HBV carriers which are roughly divided into the following 3 types.

The first type is as follows. In the case of infection via birth canal infection or during the infant stage, the immune response of the host is poor until the host is 10 to 20 years old (immune tolerance), the amount of proliferated viruses is high, HBe antigen is (+), HBe antibody is (–), and the HBV-DNA in the blood proceeds at high levels. At a certain stage, hepatocytes infected with HBV become the target of lymphocytes, and all of the hepatocytes are destroyed. However, this hepatic inflammation stage ends transiently, and the HBs antigen as a viral marker becomes seropositive. Nevertheless, there occurs the conversion of HBe antigen positive to HBe antibody positive (seroconversion), and the HBV-DNA in the blood becomes undetectable. Thereafter, the infection of HBV mutants not capable of producing HBe antigen is persistent in the liver. However, no therapeutic necessity arises in many cases due to the excellent progress of the immune tolerance and since viral growth of most of the carriers is poor, both hepatic disturbances and infectivity are also poor. The majority of the natural progress of HBV is this type.

The second type proceeds with so-called chronic hepatitis activity where the above seroconversion occurs but hepatitis is persistent.

Recently, some carriers of the second type exhibiting a change in GPT even after seroconversion to HBe antibody-positive, have drawn attention because they exhibit multiplication of HBV mutants not capable of producing HBe antigen. In these cases, carriers are seropositive to HBV-DNA persistently or intermittently, and the hepatitis is persistent which may lead to cirrhosis or heptocellular carcinoma.

The third type proceeds with HBe antigen-positive active hepatitis for 5 years or more, leading to cirrhosis or hepatocellular carcinoma.

As described above, the natural progress of HBV carriers proceeds from the HBe antigen-positive stage through the chronic hepatitis B inflammation stage to the HBe antibody-positive stage, and many of the carriers have no symptoms at the HBe antibody-positive stage. In these cases, the seronegative of HBe antigen and the seroconversion of HBe antibody indicate the sedation of chronic hepatitis B.

In some examples, however, it has been reported that cirrhosis has developed by the time of sero-conversion, and thereafter, hepatocellular carcinoma cancer may occur. In some other cases, HBe antibody-positive carriers with no symptoms may undergo severe acute exacerbation of hepatitis or persistent chronic active hepatitis.

Even in the case of HBe antibody-positive carriers with no symptoms, if cirrhosis or conditions near cirrhosis are reached in a period of hepatitis leading to the stage of being HBe antibody positive, there is the possibility that hepatocellular carcinoma occurs depending on how far along hepatic lesions have proceeded. For example, even in the case of carriers being free of symptoms for 10 years or more, there is a case where hepatocellular carcinoma occurred, and there is also a case where the hepatocellular carcinoma occurred within 1 year from initial diagnosis. Thus, even if chronic hepatitis is not active or hepatitis is not active, there is the risk hepatocellular carcinoma would occur insofar as the virus is present in the liver.

A recent study found that an apparent negative reaction to HBs antigen is observed due to genetic mutations in carriers positive to HBs antibody as the infection-protecting antibody. In this case, there is not only the seronegative HBs antigen but also the occurrence of HBs antibody. Further, the HBV is rendered resistant to HBs antibody due to the mutation of an S gene region in the HBV has been reported.

As described above, chronic hepatitis B causes various complicated conditions, as compared with hepatitis C infected similarly and causing cirrhosis or hepatocellular carcinoma.

HBV is elucidated genetically, and its conditions are elucidated in detail along with an effective diagnosis method. Therefore, a wide variety of more effective therapeutic methods have been examined.

HBV, as one kind of DNA virus, is a virus particularly liable to mutation, consequently, there are various mutants and some mutants are found to be closely related to the conditions of hepatitis B.

For example, from the study of the HBV gene, the relationship with genetic mutants observed in the transition step of seroconversion from HBe antigen to HBe antibody and the relationship between severe hepatitis and genetic mutation are also being elucidated.

Along with the elucidation of such an HBV gene, clinical significance possessed by various virus markers is also being examined to make it possible to understand the infectious state and growth condition of HBV so that a therapeutic method for the purpose of viral exclusion against HBe antigen-positive and chronic active hepatitis as described above can be examined.

The final object of chronic hepatitis B therapy is to exclude HBV completely. However, recovery from the carrier state remains almost impossible by any therapy as no accurate established method has yet been developed.

Therefore, sedation of hepatitis by reducing or inhibiting viral multiplication by antiviral therapy to induce the seroconversion of HBe antigen to HBe antibody is carried out as an effective therapeutic method under the present circumstances.

From such a viewpoint, therapy by administration of interferon (IFN) as an antiviral agent has been conducted, and for example, IFN-α or IFN-β has been used to improve viral blood disease in HBe antigen positive and DNA polymerase positive chronic active hepatitis.

The therapy of HBe antigen-positive chronic hepatitis B by administration of IFN involves administering IFN once per day or intermittently twice per week. However, it has been reported that, when IFN is administered every day for 4 weeks, seronegative HBe antigen and normalization of GPT, were almost 30% after 5 years in some therapeutic results, while seronegative HBs antigen was hardly observed. Even after IFN was administered intermittently twice per week for 8 months on average, seronegative HBe antigen and normalization of GPT were almost 45% while seronegative HBe antigen was only a few percent.

SUMMARY OF THE INVENTION

In view of these present circumstances, the present invention provides a therapeutic agent of interferon (IFN) effective against chronic hepatitis B and further provides a drug administration system for IFN therapy using said therapeutic agent as well as a therapeutic method for chronic hepatitis B by use of said administration system.

As a first embodiment of the present invention, there is provided a therapeutic agent for hepatitis B wherein IFN is divided and administered in 2 to 4 portions per day and the total dosage is a daily effective dosage of IFN.

Further, the present invention provides as a second embodiment a drug administration system (drug administration unit, drug administration method) as a means of treating chronic hepatitis B by use of said therapeutic agent, wherein the daily effective dosage of IFN is divided and administered in 2 to 4 portions per day.

By the therapeutic agent provided by the present invention, as well as by administration of IFN in the specific drug administration system using said therapeutic drug, the persistent disappearance (persistent seronegative) of HBV-DNA is observed, the seroconversion of HBe antigen to HBe antibody is induced, and the effective treatment of chronic hepatitis B with these therapeutic indications is confirmed.

Therefore, the present invention also provides as a further specific embodiment a method of inducing the seroconversion of HBe antigen to HBe antibody in the drug administration system by use of IFN in said therapeutic agent.

Further, the present invention provides a therapeutic method for the treatment of chronic hepatitis B wherein the persistent disappearance of HBV-DNA or the seroconversion of HBe antigen to HBe antibody is effectuated by the administration of IFN in said therapeutic agent.

DETAILED DESCRIPTION OF THE INVENTION

The therapeutic agent for chronic hepatitis B comprises a daily effective dosage of IFN which is divided and administered in 2 to 4 portions per day as described above; None of the prior art has examined the idea that the daily effective dosage is administered in portions, and this very unique idea has been arrived at due to the inventors' extensive examination.

IFN therapy for chronic hepatitis B has been conducted heretofore by administering IFN once per day or intermittently for several days, however, under the prior art system, the degree of seronegative HBe antigen is not so high. The reason for the low degree of seronegative HBe may be because the amount of hepatitis B virus is significantly high such that short-term administration of IFN may not bring about a sufficient level of IFN for eliminating the HBe antigen. On the other hand, the reason for the higher normalization degrees achieved by intermittently administrating IFN, rather than by administrating it once per day, may be due to the use of a small dosage of IFN for a long period of time.

Accordingly, it is more effective for treatment of chronic hepatitis B to permit IFN to remain in the liver for a relatively long period. Hence, the therapeutic agent of the present invention can be very effective for treatment of chronic hepatitis B.

In fact, the daily effective dosage of IFN administered several times per day by use of the therapeutic agent provided by the present invention, in

What we claim is:

1. A method for the persistent negation of HBV-DNA or for inducing the seroconversion of HBe antigen to HBe antibody or for treating hepatitis B comprising administering a daily effective dose of interferon-$\beta$ (IFN-$\beta$), wherein the daily effective dose is administered in two portions for four weeks.

2. A method for the persistent negation of HBV-DNA or for inducing the seroconversion of HBe antigen to HBe antibody or for treating hepatitis B comprising administering a daily effective dose of interferon-$\beta$ (IFN-$\beta$), wherein the daily effective dosage of IFN-$\beta$ is administered in a plurality of individual doses per day for a predetermined number of days, and subsequently administered in one portion per day.

3. A method according to claim 1 wherein the daily effective dose of IFN-$\beta$ is divided and administered in 2 to 4 portions per day for 1 to 4 weeks followed by one portion each day for the following 1 to 4 weeks.

4. A method according to claim 1 wherein the daily effective dose of IFN-$\beta$ is divided and administered in 2 to 4 portions per day for 1–4 weeks followed by one portion of the daily effective dose administered three 3 times per week for 4 weeks.

5. A method according to any one of claims 2 to 4 where the two step administration system is repeated.

6. A method according to claim 5 wherein the daily effective dose of IFN-$\beta$ is 3 to 6 million units.

* * * * *

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

<u>Column 4,</u>
Lines 24-26, paragraph should read as follows:

In fact, the daily effective dosage of IFN administered several times per day by use of the therapeutic agent provided by the present invention, in place of the conventional administration of IFN conducted once per day or intermittently for several days, showed improved seroconversion of HBe antigen to HBe antibody along with the persistent disappearance of HBV-DNA.

In particular, it was revealed that the specific administration system of the present invention is more effective against active chronic hepatitis B caused by HBV mutants.

The daily dosage of IFN administered in portions by use of the therapeutic agent provided by the present invention may be that of clinically used conventional IFN-β or IFN-β. Administration of IFN-β is more preferable among these agents, and accordingly the present invention provides a therapeutic agent wherein IFN-β can be divided and administered in 2 to 4

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd),

```
portions per day, the total dosage as the daily effective
dosage of IFN, and the drug administration system using said
therapeutic agent.
     The frequency of administration of the daily effective
dosage of IFN per day is not particularly limited.  The
frequency is selected such that chronic hepatitis B, as the
object, can be reliably cured by said administration and
therefore, the frequency is determined depending on the type
of IFN and the condition of the patient.  Preferably,
administration is conducted about 2 to 4 times per day, more
preferably 2 or 3 times per day.
     Too frequent administration causes a high burden on the
patient and a diminished dosage with each administration.
This can result in a failure to demonstrate its effects.
     The daily effective dosage of IFN is also not limited.
The daily effective dosage used generally for treatment of
chronic hepatitis B can be selected suitably, for example,
within 3- to 18-million units for IFN-β and 3- to 6-million
units for IFN-β.  For more effective therapy, the maximum of
the daily effective dosage is preferred, therefore, 18-million
units and 6-million units are preferable for IFN-β and IFN-β
respectively.
     By administration of the therapeutic agent of the present
invention, persistent seronegative HBV-DNA is observed at a
relatively early stage.  Therefore, the therapeutic agent of
the invention is administered every day preferably for 1 to 4
```

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd), weeks, more preferably for 4 weeks during which the persistent disappearance of HBV-DNA is achieved.

Accordingly, the preferred administration system of the first embodiment of the invention using the therapeutic agent, is a drug administration regimen wherein the daily effective dosage of IFN-β (3- to 6-million units) is divided and administered in 2 to 4 portions per day, and said daily effective dosage is administered every day for 1 to 4 weekspreferably 4 weeks.

The drug administration system for IFN, as used against chronic hepatitis B, in the therapeutic agent of the present invention and the persistent disappearance of HBV-DNA by said system using IFN-β as IFN, is described in more detail by reference to the following examples.

It should be noted that the basic administration system for any other kinds of IFN is the same as that for the IFN-β case described below except for the dosage.

The daily effective dosage of IFN-β approved at present in the world ranges from 3- to 6-million units. The antiviral effect achieved by administration of IFN is said to be in proportion to the dosage. Accordingly, considering that hepatitis B is an infection caused by HBV, the maximum dosage of 6-million units per day, the effective daily dosage in the present invention, is used for the effective suppression of tissues infected with HBV; said dosage is preferably divided and administered in 2 to 4 portions per day. The dosage can

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd), be selected within the range of 3- to 6-million units as the daily effective dosage, depending on the amount of the virus and the severity of the disease in the patient to be treated.

As an example, in one case, 6-million units of IFN-□ was divided into 2 portions and each portion was administered through intravenous drip infusion in the morning and evening. The administration of this daily effective dosage of IFN in portions was performed every day for 4 weeks, and as a result, the disappearance of HBV-DNA was observed at an early stage after administration was initiated. Also the state of this disappearance was persistent for a prolonged period of time, while the conversion (sero-conversion) of HBe antigen to HBe antibody was induced, thus indicating that this administration was also effective against the case of chronic hepatitis B caused by so-called HBV mutants.

Among chronic hepatitis B, silent hepatitis B (hepatitis whose viral marker, particularly HBs antibody, does not become positive even though infected with hepatitis B virus) is regarded as problematic. However, it has been revealed that the specific administration method of the invention is effective against silent chronic hepatitis B caused by a wide variety of such HBV gene mutants.

The ultimate object of chronic hepatitis B therapy lies in complete exclusion of HBV (recovery from the carrier state), however, under the present conditions, where therapeutic expulsion of HBV is almost impossible, the

UNITED STATES PATENT AND TRADEMARK OFFICE
CERTIFICATE OF CORRECTION

PATENT NO.    : 6,667,033 B1
DATED         : December 23, 2003
INVENTOR(S)   : Hiroaki Okushin It is certified that error appears in the above-identified patent and that said Letters Patent is hereby corrected as shown below:

Column 4 (cont'd), persistent disappearance of HBV-DNA can still be achieved by administering the therapeutic agent of the present invention which inhibits the multiplication of the virus and effectively induces seroconversion. Accordingly, the present invention can be said to be effective as a method of treating the conditions of a wide variety of chronic hepatitis B mutants.

As described above, the present invention provides a method of administering IFN as a therapeutic agent for chronic hepatitis B, where successive administration for 1 to 4 weeks is performed in the system and where the daily effective dosage of IFN is divided and administered in portions, thereby effectuating the persistent disappearance of HBV-DNA. After such administration is carried out, additional administrations of the daily effective dosage of IFN can be conducted daily or intermittently for continued persistent antiviral effect. It has been found that a continued excellent therapeutic effect can be achieved by suitably repeating this administration cycle.

The present invention provides as an additional embodiment, a drug administration system for treating chronic hepatitis B wherein the daily effective dosage of IFN is divided and administered in 2 to 4 portions per day for 1 to 4 weeks, preferably 4 weeks, followed by administration of the daily effective dosage once per day in succession or intermittently for 1 to 4 weeks. The IFN used therein may be IFN-β or IFN-β. As a more specific embodiment, the present

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd), invention provides a method of inducing the seroconversion of HBe antigen to HBe antibody by use of said drug administration system (drug administration unit) of IFN, as well as a therapeutic method for the treatment of chronic hepatitis B by use of the system.

Considering that IFN-β is the preferred IFN for initial administration several times per day, it follows that it is also preferable to use IFN-β in the subsequent administration conducted once per day. The IFN, of course, should be suitably selected depending on the condition of the patient in question.

The actual treatment of the administration system of the present invention is described in detail as follows.

In one embodiment of the invention, as an example, 6-million units as the daily dosage of IFN-β was divided into 2 portions, and each portion, i.e., 3-million units, was dissolved in 100 ml of 5 % glucose solution. The portions were administered twice per day (total of 6-million units/day) via intravenous drip infusion in the morning and evening (e.g. 9:00 a.m. and 7:00 p.m.) for 30 minutes, and this administration was performed every day for 4 weeks.

HBV-RNA became seronegative after the initial administration of IFN-β was conducted several times per day. Following this initial administration, 6-million units, as the daily effective dosage of IFN-β, was dissolved in 100 ml of 5 % glucose solution and administered once per day via

UNITED STATES PATENT AND TRADEMARK OFFICE
CERTIFICATE OF CORRECTION

PATENT NO.  : 6,667,033 B1
DATED       : December 23, 2003
INVENTOR(S) : Hiroaki Okushin It is certified that error appears in the above-identified patent and that said Letters Patent is hereby corrected as shown below:

Column 4 (cont'd), intravenous drip infusion for 30 minutes in the morning (9:00). This additional administration was conducted every day for 4 weeks.

Alternatively, 18-million units as the daily effective dosage of IFN-β, in place of IFN-β, may be intramuscularly administered once per day, and this administration may be conducted intermittently 3 times per week.

Additionally, 6-million units as the daily effective dosage of IFN-β can be intravenously administered once a day, intermittently 3 times per week.

By the subsequent administration conducted once per day, HBV-DNA was kept negative and positive reaction to HBe antibody was observed.

Subsequently, IFN-β was further administered twice per day for 4 weeks, followed by administration once per day for an additional 4 weeks.

As a result of this administration regime, the persistent disappearance of HBV-DNA was observed for a prolonged period of time after the whole administration of IFN-β was completed and the seroconversion of HBe antigen to HBe antibody was induced. In the subsequent diagnosis, the recurrence of hepatitis B was not observed, and neither was the transition to cirrhosis etc.

Accordingly, the present invention provides as another embodiment, a drug administration system wherein the daily effective dosage of IFN-β is divided and administered in 2 to

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

<u>Column 4 (cont'd),</u>

4 portions, preferably in 2 portions, and said administration, in 2 to 4 portions, is conducted every day for 1 to 4 weeks, preferably for 4 weeks. Subsequently, the daily effective dosage of IFN-β (or IFN-β) is administered once per day in succession or intermittently for 1 to 4 weeks, preferably for 4 weeks, and if necessary, the complete administration cycle, consisting of 2 to 4 portions for 1 to 4 weeks followed by one dose per day in succession or intermittently for 1 to 4 weeks, is further repeated. In this manner, the present invention describes a method for the persistent disappearance of HBV-DNA by the said drug administration system as well as a therapeutic method for the treatment of chronic hepatitis B by inducing the seroconversion of HBe antigen to HBe antibody.

The actual therapy using the therapeutic agent of the present invention is described by reference to the following Examples.

1. Therapeutic Example (No. 1):

On Day 1, 3-million units of IFN-β was divided into 1-million and 2-million units, and administered to a patient with chronic hepatitis B (age: 24 years old, female) at 9:00 in the morning and 7:00 in the evening via intravenous drip infusion. On Days 2 through 7, 6-million units were divided into two 3-million unit portions and each portion was administered via intravenous drip infusion at 9:00 in the morning and at 7:00 in the evening. For 3 weeks thereafter, 3-million units were divided into three 1-million unit

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd), portions and each portion was administered via intravenous drip infusion at 9:00 in the morning, 2:00 in the afternoon, and 7:00 in the evening. The therapy was thus carried out for 4 weeks in total using the therapeutic agent of the present invention.

To determine the effectiveness of the chronic hepatitis B therapy, the following were examined: GPT levels as an indicator of hepatic functions, HBe antigen and Hbe antibody, and HBV-DNA polymerase.

Initial Levels Examined when Therapy was Initiated:

GTP levels: 438 U/L; seropositive of HBe antigen and seronegative of HBe antibody; HBV-DNA polymerase: 1338 cpm.

When the therapeutic agent of the present invention was administered for 4 weeks, GPT levels were reduced to the normal level of 19 U/L after 3 months from the administration, and remained at the normal level of 11 U/L even after 12 months from the administration. Further, seroconversion was induced after 6 months from the administration and the persistent disappearance of HBV-DNA continued, indicating good treatment of chronic hepatitis B.

The therapy using the therapeutic agent of the present invention was conducted for other patients with chronic hepatitis B, and good reduction in GPT levels, as an indication of hepatic functions, was observed in all cases after administration.

Further, the persistent disappearance of HBV-DNA

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd),

```
continued in a few cases of the patients treated, and the
induction of the seroconversion of HBe antigen to HBe antibody
was observed at an early stage.
     In these therapeutic examples, the recurrence of
hepatitis B was not observed in diagnoses conducted
thereafter.

2. Therapeutic Example (No. 2):
(a) Method:
     The progress of patients treated with IFN was observed
for 1 year or more.  Nine patients with chronic hepatitis B
were chosen as the subjects (7 male patients, 2 female
patients: 24 to 48 years old, 32.0 years old on average).
Prior to treatment, examination showed that the nine subjects
were positive for HBe antigen, HBV-DNA (by the  bDNA probe
method), and HBV-DNA polymerase (DNA-P).
     The examination of the 9 patients before therapy
indicated 5 cases where HBV-DNA polymerase was less than 1,000
cpm and 4 cases where the polymerase was 1,000 cpm or more.
All the cases were strongly seropositive for HBc antibody
(x200) and seronegative for HCV antibody.
     Administration of the therapeutic agent of the present
invention was carried out by administering it in portions for
4 weeks as follows.
(A) First week:
     Till Day 7, IFN-β was divided in 2 portions per day and
```

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd), administered at 9:00 in the morning and 7:00 in the evening. The dosage on the first day was 3-million units consisting of 1-million units in the morning and 2-million units in the evening. The daily dosage for the following 6 days was 6-million units consisting of 3-million units each in the morning and evening.

(B) Subsequent 3 weeks:

On the 8th day and thereafter, a total daily dosage of 3 million units of IFN-$\beta$ was divided to 3 portions of 1 million units and administered in the morning at 6:00, during the afternoon at 2:00, and in the night at 10:00.

For administration, 100 ml of 5 % glucose solution containing IFN-$\beta$ was administered via intravenous drip infusion with the administration time for each 1-million unit dose being 10 minutes.

(b) Results:

During administration of IFN-$\beta$ as the therapeutic agent of the present invention, subjective symptoms (general dullness, poor appetite, depression etc.) were slight.

The reduction in platelets or protein (1+; 1 case: 2+; 2 cases) during the administration did not cause the administration of the therapeutic agent of the present invention, administered in portions for 4 weeks, to be discontinued in every case.

GPT varied during the administration of IFN-$\beta$ and there was no normalized example when the administration was

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd),

```
finished.  However, although acute exacerbation occurred
during or after the administration, persistent normalization
of GPT for 6 months was achieved in 5 out of 9 cases (55.6
%)with these 5 cases judged to be significantly effective.
     The viral examination of these 5 significant cases,
conducted 1 year after the administration of IFN-β, is as
follows:
     In 5 cases, the HBV-DNA polymerase was negative (less
than 20 cpm).
     In 4 cases, HBV-DNA (bDNA probe method) was less than the
limit of detection (less than 0.70 Meq/ml) and in the
remaining 1 case, it was as low as 0.85 Meq/ml.
     With respect to the significant efficacy for HBV-DNA
polymerase examined before administration of the therapeutic
agent of the present invention, 4 out of 5 cases indicated
levels less than 1,000 cpm and 1 case out of 4 cases indicated
levels more than 1,000 cpm.
     The majority of HBV carriers with chronic hepatitis B
have no symptoms and do not require antiviral therapy.
Nevertheless, even if HBe antigen disappears in the case of
hepatitis caused by HBV mutants, the virus still remains
insofar as the disappearance of HBs antigen is observed thus
indicating a high risk of cirrhosis transition to
hepatocellular carcinoma.
      Given that the effective persistent disappearance of HBV-
DNA can be achieved by the specific administration system of
```

UNITED STATES PATENT AND TRADEMARK OFFICE
CERTIFICATE OF CORRECTION

PATENT NO. : 6,667,033 B1
DATED : December 23, 2003
INVENTOR(S) : Hiroaki Okushin It is certified that error appears in the above-identified patent and that said Letters Patent is hereby corrected as shown below:

Column 4 (cont'd),

```
    the present invention, it can be said that the present
invention is particularly effective for treatment of
complicated chronic hepatitis B.
    As described above, the present invention provides a
specific therapeutic agent for treatment of chronic hepatitis
B by IFN, as well as an administration system using said
therapeutic agent (administration method, administration
unit). According to said administration system,
seroconversion is efficiently induced, thus giving rise to the
persistent disappearance of HBV-DNA and the resultant
treatment of chronic hepatitis B.
    In this respect, the therapeutic agent of the present
invention gives a new guideline for a preferred therapy for
the treatment of chronic hepatitis B by IFN, thus making a
great contribution to the medical practice.
```

Signed and Sealed this

Thirty-first Day of August, 2004

JON W. DUDAS
*Director of the United States Patent and Trademark Office*